United States Patent [19]

Breuer et al.

[11] Patent Number: 4,499,016
[45] Date of Patent: Feb. 12, 1985

[54] 2-OXO-1-[(ACYLAMINO)SULFONYL]AZETIDINES

[75] Inventors: Hermann Breuer, Schoenhofen; Theodor Denzel; Uwe D. Treuner, both of Regensburg, all of Fed. Rep. of Germany

[73] Assignee: E. R. Squibb & Sons, Inc., Princeton, N.J.

[21] Appl. No.: 290,648

[22] Filed: Aug. 6, 1981

[51] Int. Cl.$^3$ .................. C07D 205/08; C07D 417/12; A61K 31/425; A61K 31/395
[52] U.S. Cl. ............................... 260/239 A; 260/245.4
[58] Field of Search ..................... 260/245.4, 239 A

[56] References Cited

FOREIGN PATENT DOCUMENTS 0021678 1/1981 European Pat. Off. .
54-72813 12/1980 Japan .

OTHER PUBLICATIONS

Angew. Chem. Internat. Edit., 7(3): 172, (1968).

Primary Examiner—Mark L. Berch
Attorney, Agent, or Firm—Lawrence S. Levinson; Donald J. Barrack

[57] ABSTRACT

Antibacterial activity is exhibited by β-lactams having an —SO$_2$—NH—C—R substituent in the 1-position and an acylamino substituent in the 3-position wherein R is alkyl, phenyl, substituted phenyl, phenylalkyl, (substituted phenyl)alkyl, alkoxy, phenyloxy, (substituted phenyl)oxy, phenylalkoxy, or (substituted phenyl)alkoxy.

7 Claims, No Drawings

2-OXO-1-[(ACYLAMINO)SULFONYL]AZETIDINES

RELATED APPLICATIONS

U.S. patent application Ser. No. 226,562, filed Jan. 19, 1981, discloses β-lactam antibiotics having a sulfonic acid salt (—SO$_3^\ominus$M$^\oplus$; M$^\oplus$ is a cation) in the 1-position and an acylamino substituent in the 3-position.

U.S. patent application Ser. No. 202,830, filed Oct. 31, 1980, now U.S. Pat. No. 4,337,197, issued June 29, 1982, discloses β-lactam antibiotics having a sulfate (—O—SO$^\ominus$M$^\oplus$; M$^\oplus$ is a cation) substituent in the 1-position and an acylamino substituent in the 3-position.

U.S. patent application Ser. No. 252,672, filed Apr. 9, 1981, now abandoned discloses β-lactam antibiotics having an acylamino substituent in the 3-position and a

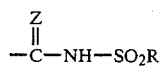

substituent in the 1-position, wherein Z is oxygen or sulfur and R is alkyl, alkenyl, alkynyl, substituted alkyl, phenyl, substituted phenyl, heteroaryl, phenylalkyl, (substituted phenyl)alkyl, (heteroaryl)alkyl or —N-R$_a$R$_b$ wherein R$_a$ and R$_b$ are the same or different and each is hydrogen, alkyl, substituted alkyl, phenyl, substituted phenyl, heteroaryl, phenylalkyl, (substituted phenyl)alkyl, or (heteroaryl)alkyl, or one or R$_a$ and R$_b$ is hydrogen, alkyl, phenyl or substituted phenyl, and the other is amino, alkanoylamino, alkylamino, dialkylamino, phenylamino, (substituted phenyl)amino, hydroxy, cyano, alkoxy, phenyloxy, (substituted phenyl)oxy, phenylalkoxy, (substituted phenyl)alkoxy, (heteroaryl)alkoxy, alkylmethyleneamino, phenylmethyleneamino, or (substituted phenyl)methyleneamino, or R$_a$ and R$_b$ together with the nitrogen atom to which they are attached form a 5,6, or 7-membered fully or partially saturated ring optionally containing additional nitrogen, oxygen or sulfur atoms.

BACKGROUND OF THE INVENTION

The β-lactam ring,

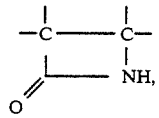

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism *Penicillium notatum* had antibiotic properties. The compound which Fleming had worked with was benzylpenicillin,

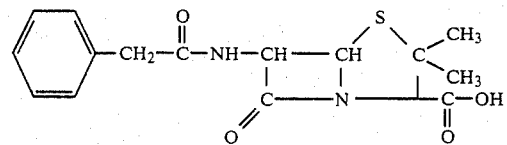

The in vivo activity of benzylpenicillin against various bacteria was reported by Chain et al. in Lancet, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

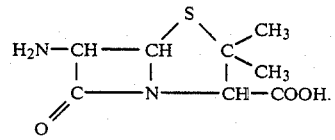

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C,

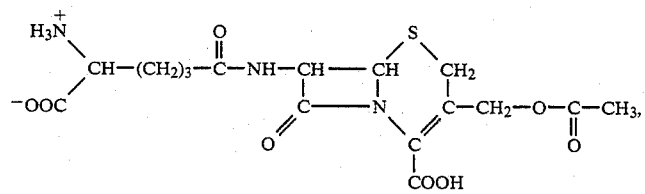

proved to be an important stepping stone in cephalosporin research. Removal of the acyl group in the 7-position of cephalosporin C yields 7-aminocephalosporanic acid,

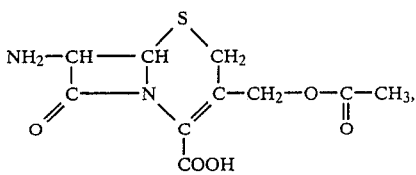

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

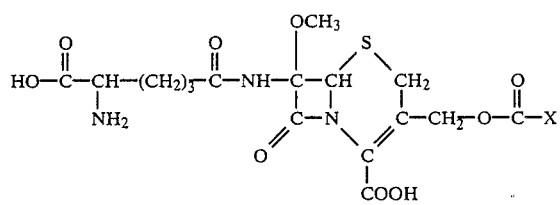

cephamycin A: X = 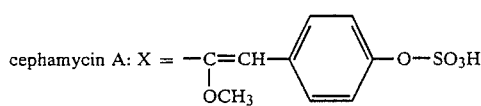

cephamycin B: X = 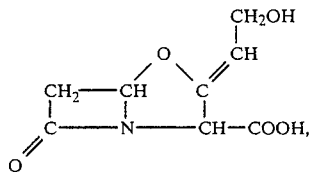

cephamycin C: X = —NH₂.

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII (1):1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

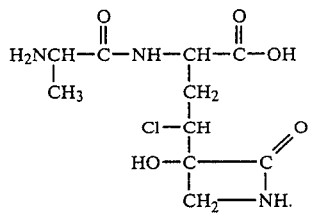

The structure of the above naturally occurring monocyclic β-lactam containing molecule is similar to the structure of the earlier discovered β-lactam containing molecules known as tabotoxins, i.e.,

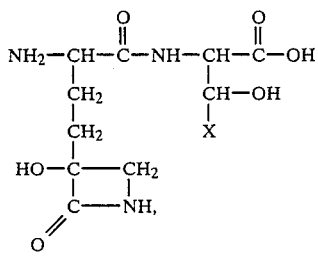

wherein X is hydrogen or methyl as reported by Stewart, *Nature*, 229:174 (1971), and Taylor et al., *Biochem. Biophys. Acta.*, 286:107 (1972).

Recently, several novel series of naturally occurring β-lactam antibiotics have been isolated. The nocardicins, nocardicin A and B, are monocyclic β-lactams having the formula

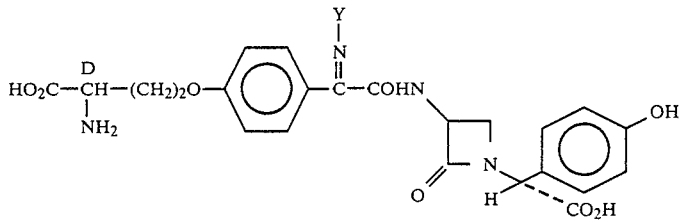

nocardicin A: Y=—syn(Z)OH
nocardicin B: Y=—anti(E)OH, as reported by Hishimoto et al., *The Journal of Antibiotics*, XXIX (9):890 (1976).

Clavulanic acid, a bicyclic β-lactam antibiotic isolated from fermentation broths of *Streptomyces clavuligerus*, has the formula i.e., Z-(2R,5R)-3-(β-hydroxyethylidene)-7-oxo-4-oxa-1-azabicyclo[3,2,0]heptane-2-carboxylic acid, as reported by Lloyd et al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers-Schonberg et al., *J.A.C.S.*, 100:20, 6491 (1978), thienamycin has the structure

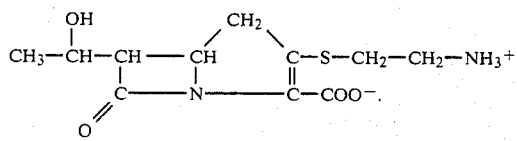

Additional fused β-lactams, olivanic acid derivatives, have recently been isolated from cultures of *Streptomyces olivaceus*. As disclosed by Brown et al., *J.C.S. Chem. Comm.*, these olivanic acid derivatives have the formulas

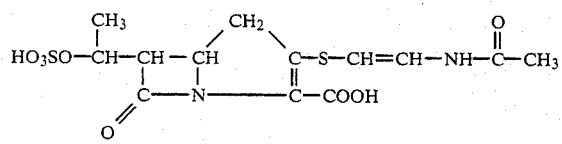

and

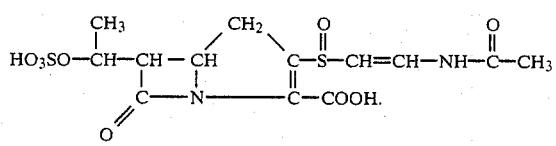

The isolation of the above antibiotics, and a discussion of their activity, is reported by Butterworth et al., *The Journal of Antibiotics*, XXXII (4):294 (1979) and by Hood et al., *The Journal of Antibiotics*, XXXII (4):295 (1979).

Another recently isolated β-lactam antibiotic is PS-5, reported by Okamura et al., *The Journal of Antibiotics*, XXXI: 480 (1978) and *The Journal of Antibiotics*, XXXII (4):262 (1979). The structure of this antibiotic, which is produced by *Streptomyces cremeus* subspecies *auratilis*, is reported to be

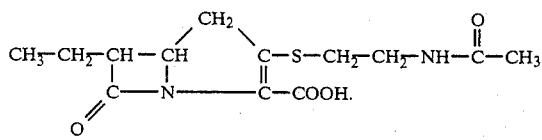

Structurally related antibiotics PS-6 and PS-7 are reported in European Patent application Ser. No. 1,567 to have the respective structures

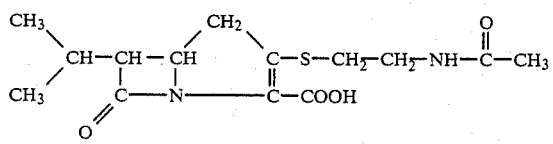

and

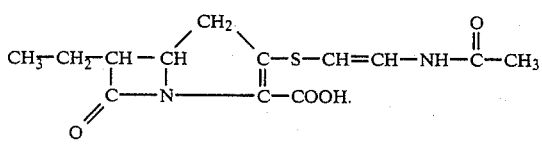

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a substituent having the formula

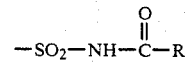

attached to the nitrogen atom in the nucleus.

β-Lactams having the formula

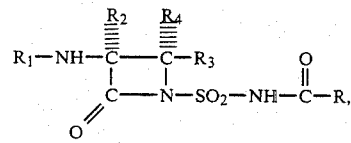

and salts thereof, exhibit activity against a range of gram-negative and gram-positive bacteria.

β-Lactams having the formula

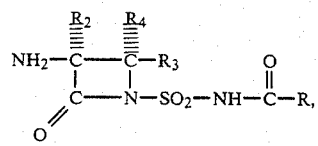

and salts thereof, are intermediates useful for the preparation of corresponding 3-acylamino compounds.

As used in formulas I and II, and throughout the specification, the symbols are as defined below.

R is alkyl, phenyl, substituted phenyl, phenylalkyl, (substituted phenyl)alkyl, alkoxy, phenyloxy, (substituted phenyl)oxy, phenylalkoxy, or (substituted phenyl)alkoxy;

$R_1$ is acyl;

$R_2$ is hydrogen or methoxy;

$R_3$ and $R_4$ are the same or different and each is hydrogen or alkyl.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The terms "alkanoyl" and "alkenyl" refer to both straight and branched chain groups. Those groups having 2 to 10 carbon atoms are preferred.

The term "halogen" refers to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino(—NH$_2$), halogen, hydroxyl, trifluoromethyl, alkyl (of 1 to 4 carbon atoms), alkoxy (of 1 to 4 carbon atoms) or carboxyl groups.

The term "acyl" includes all organic radicals derived from an organic acid (i.e., a carboxylic acid) be removal of the hydroxyl group. Certain acyl groups are, of course, preferred but this preference should not be viewed as a limitation of the scope of this invention. Exemplary acyl groups are those acyl groups which have been used in the past to acylate $\beta$-lactam antibiotics including 6-aminopenicillanic acid and derivatives and 7-aminocephalosporanic acid and derivatives; see, for example, *Cephalosporins and Penicillins,* edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula $$R_5-\overset{O}{\underset{\|}{C}}-$$

wherein $R_5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

[structure with $R_6$, $R_7$, $R_8$, $(CH_2)_n-C(=O)-$]

[structure with $R_6$, $R_7$, $R_8$, $CH(R_9)-C(=O)-$]

[structure with $R_6$, $R_7$, $R_8$, $CH_2-O-C(=O)-$]

[structure with $R_6$, $R_7$, $R_8$, $O-CH_2-C(=O)-$]

[structure with $R_6$, $R_7$, $R_8$, $S-CH_2-C(=O)-$ or]

[structure with $R_6$, $R_7$, $R_8$, $CH_2-S-C(=O)-$]

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_9$ is amino, hydroxyl, a carboxyl salt, protected carboxyl, formyloxy, a sulfo salt, a sulfonamino salt, azido, halogen, hydrazino, alkylhydrazino, phenylhydrazino, or [(alkylthio)thioxomethyl]thio.

Preferred carbocyclic aromatic acyl groups include those having the formula

[HO-phenyl-$CH_2-C(=O)-$,]

[phenyl(CH_2NH_2)-$CH_2-C(=O)-$,]

[HO-phenyl-$CH(R_9)-C(=O)-$]

($R_9$ is preferably a carboxyl salt or sulfo salt) and

[phenyl-$CH(R_9)-C(=O)-$]

($R_9$ is preferably a carboxyl salt or sulfo salt).

(c) Heteroaromatic groups having the formula $$R_{10}-(CH_2)_n-\overset{O}{\underset{\|}{C}}-,$$

$$R_{10}-\underset{R_9}{\underset{|}{CH}}-\overset{O}{\underset{\|}{C}}-,$$

$$R_{10}-O-CH_2-\overset{O}{\underset{\|}{C}}-,$$

$$R_{10}-S-CH_2-\overset{O}{\underset{\|}{C}}-\text{ or}$$

$$R_{10}-\overset{O}{\underset{\|}{C}}-\overset{O}{\underset{\|}{C}}-,$$

wherein n is 0, 1, 2 or 3; $R_9$ is as defined above; and $R_{10}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

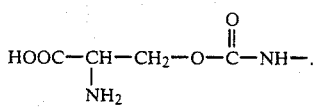

Preferred heteroaromatic acyl groups include those groups of the above formulas wherein $R_{10}$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

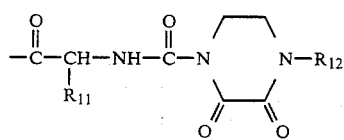

wherein $R_{11}$ is an aromatic group (including carbocyclic aromatics such as those of the formula

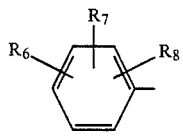

and heteroaromatics as included within the definition of $R_{10}$); and $R_{12}$ is alkyl, substituted alkyl (wherein the alkyl group is substituted with one or more halogen, cyano, nitro, amino or mercapto groups), arylmethyleneamino (i.e., —N=CH—$R_{11}$ wherein $R_{11}$ is as defined above), arylcarbonylamino (i.e.,

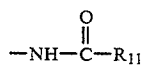

wherein $R_{11}$ is as defined above) or alkylcarbonylamino.

Preferred [[(4-substituted-2,3-dioxo-1-piperazinyl)carbonyl]amino]arylacetyl groups include those wherein $R_{12}$ is ethyl, phenylmethyleneamino or 2-furylmethyleneamino.

(e) (Substituted oxyimino)arylacetyl groups having the formula

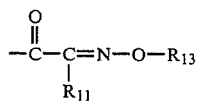

wherein $R_{11}$ is as defined above and $R_{13}$ is hydrogen, alkyl, cycloalkyl, alkylaminocarbonyl, arylaminocarbonyl (i.e.,

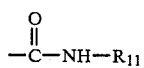

wherein $R_{11}$ is as defined above) or substituted alkyl (wherein the alkyl group is substituted with 1 or more halogen, cyano, nitro, amino, mercapto, alkylthio, aromatic group (as defined by $R_{11}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_{11}$ is 2-amino-4-thiazolyl. Also preferred are those groups wherein $R_{13}$ is methyl, ethyl, carboxymethyl, 1-carboxy-1-methylethyl or 2,2,2-trifluoroethyl.

(f) (Acylamino)arylacetyl groups having the formula

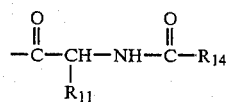

wherein $R_{11}$ is as defined above and $R_{14}$ is

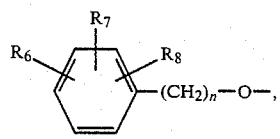

amino, alkylamino, (cyanoalkyl)amino, amido, alkylamido, (cyanoalkyl)amido,

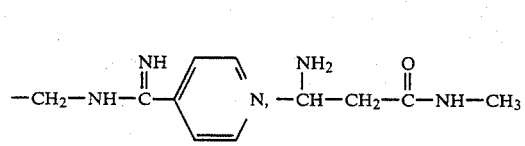

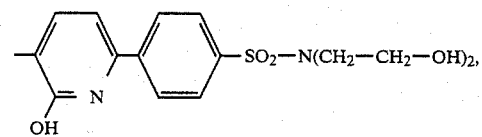

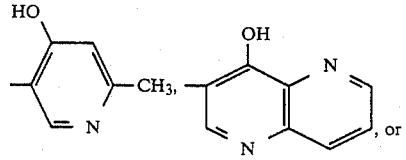

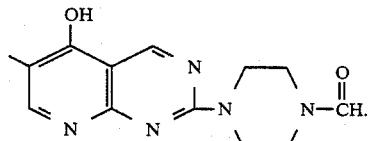

Preferred (acylamino)arylacetyl groups of the above formula include those groups wherein $R_{14}$ is amino or amido. Also preferred are those groups wherein $R_{11}$ is phenyl or 2-thienyl.

(g) [[[3-Substituted-2-oxo-1-imidazolidinyl]carbonyl]amino]arylacetyl groups having the formula

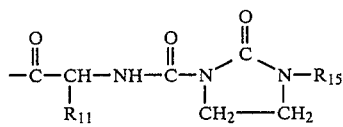

wherein $R_{11}$ is as defined above and $R_{15}$ is hydrogen, alkylsulfonyl, arylmethyleneamino (i.e., $-N=CH-R_{11}$ is as defined above),

(wherein $R_{16}$ is hydrogen, alkyl or halogen substituted alkyl), aromatic group (as defined by $R_{11}$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_{11}$ is phenyl or 2-thienyl. Also preferred are those groups wherein $R_{15}$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having an

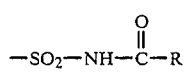

substituent in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

With respect to the β-lactams of formulas I and II, the structural formulas have been drawn to show the stereochemistry at the chiral center in the 3-position.

Also included within the scope of this invention are racemic mixtures which contain the above-described β-lactams.

DETAILED DESCRIPTION OF THE INVENTION

β-Lactams having an

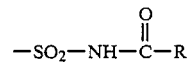

substituent in the 1-position of the β-lactam nucleus and an acylamino substituent in the 3-position of the β-lactam nucleus, and salts thereof, have activity against a range of gram-negative and gram-positive organisms.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

An

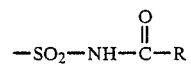

activating group can be introduced onto the nitrogen atom of a β-lactam nucleus by first silylating the β-lactam to yield the corresponding 1-substituted silyl derivative. Exemplary silylating agents are monosilyltrifluoroacetamide, trimethylsilylchloride/triethylamine, and bis-trimethylsilyltrifluorocetamide. The reaction is preferably run in an inert organic solvent.

The resulting 1-silylated-2-azetidinone is reacted with an isocyanate having the formula $$Y-SO_2-N=C=O, \qquad III$$

wherein Y is a leaving group, preferably a halogen, and then with the appropriate carboxylic acid having the formula

wherein $R_c$ is alkyl, phenyl, substituted phenyl, or phenylalkyl, or (substituted phenyl)alkyl, yields the corresponding β-lactam having an activating group of the formula

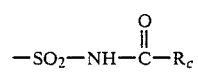

in the 1-position.

Reaction of a 1-silylated-2-azetidinone with an isocyanate of formula III followed by reaction with the appropriate alcohol having the formula

wherein $R_d$ is alkoxy, phenyloxy, (substituted phenyl)oxy, phenylalkoxy, or (substituted phenyl)alkoxy, yields the corresponding β-lactam having an activating group of the formula

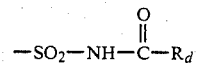

in the 1-position.

Alternatively, an isocyanate of formula III can first be reacted with a carboxylic acid of formula V or an alcohol of formula VI and the resulting product reacted with a 1-silylated-2-azetidinone to yield a β-lactam having a group of the formula

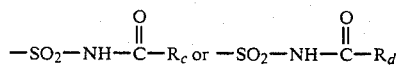

in the 1-position.

Still another alternative comprises the reaction of a 1-silylated-2-azetidinone with an isocyanate of formula III and water, or with an aminosulfonyl halide, to yield a 2-azetidinone having an aminosulfonyl group in the 1-position. Reaction of a 1-(aminosulfonyl)-2-azetidinone with an isocyanate having the formula $R_a$—NCO ($R_a$ is hydrogen, alkyl, phenyl, substituted phenyl, phenylalkyl or (substituted phenyl)alkyl) and base yields the corresponding β-lactam having a group of the formula

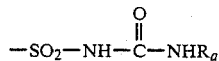

in the 1-position. Silylation of a 1-(aminosulfonyl)-2-azetidinone (or removal of a proton from the aminosulfonyl group) followed by reaction with an acid halide of the formula

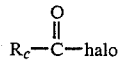

yields the corresponding β-lactam having an activating group

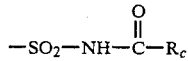

in the 1-position.

The β-lactams of formula I wherein $R_2$ is hydrogen can be prepared from a 3-protected amino-2-azetidinone having the formula

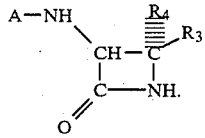      VII

In formula VII, and throughout the specification, the symbol "A" refers to an amino protecting group. These groups are well known in the field of β-lactam chemistry, and the particular group chosen is not critical. Benzyloxycarbonyl, trityl, and t-butoxycarbonyl are exemplary protecting groups.

The addition of an

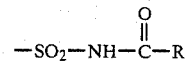

activating group to a compound of formula VII (using the procedures described above) yields a compound having the formula

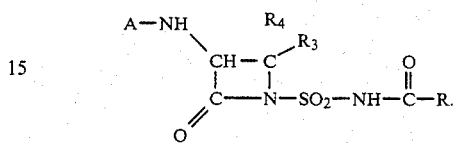      VIII

Deprotection of a compound of formula VIII using conventional techniques yields the corresponding key intermediate having the formula

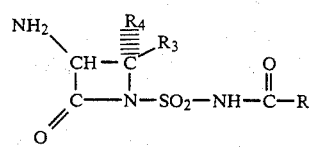      IX or a salt thereof. The particular deprotection reaction used will, of course, depend on the protecting group ("A") present. If, for example, A is a t-butoxycarbonyl protecting group, deprotection can be accomplished by treatment of a compound of formula IX with acid (e.g., formic acid or trifluoroacetic acid). If, for example, A is a benzyloxycarbonyl protecting group, deprotection can be accomplished by catalytic hydrogenation of a compound of formula VIII. Trimethylsilyl iodide is also useful for the removal of benzyloxycarbonyl and t-butoxycarbonyl protecting groups.

Well known acylation techniques can be used to convert an intermediate of formula IX to a corresponding product of formula I. Exemplary techniques include reaction of a compound of formula IX with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

An alternative procedure for preparing the compounds of formula I wherein $R_2$ is hydrogen comprises first acylating (acylation techniques have been described above) a 3-amino-2-azetidinone having the formula

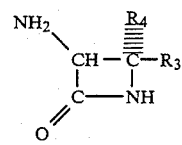      X to yield an intermediate having the formula

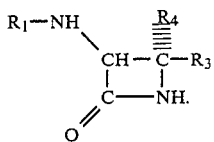

An

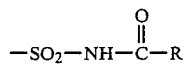

activating group can be introduced in the 1-position of a compound of formula XI (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I wherein $R_2$ is hydrogen comprises the use of a 3-azido-2-azetidinone having the formula

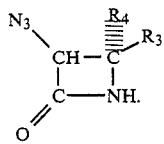

An

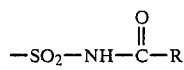

activating group can be introduced in the 1-position of a compound of formula XII (using the procedures described above) to obtain the corresponding compound having the formula

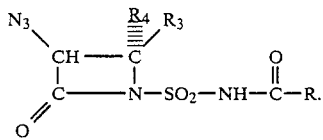

The compounds of formula XIII are novel intermediates, and as such, they constitute an integral part of this invention.

Reduction of an intermediate of formula XIII yields the corresponding intermediate having the formula

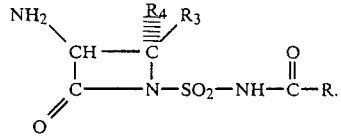

The reduction can be accomplished by catalytic (e.g., palladium on charcoal or platinum oxide) hydrogenation or with reducing agents such as zinc or triphenylphosphine. As described above, from these key intermediates (compounds of formula IX), using conventional acylation techniques, it is possible to prepare all of the products of formula I wherein $R_2$ is hydrogen.

Alternatively, a 3-azido-2-azetidinone of formula XII can be reduced to the corresponding 3-amino-2-azetidinone having the formula

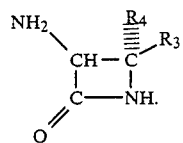

The reduction can be accomplished by catalytic (e.g., palladium on charcoal or platinum oxide) hydrogenation or with reducing agents such as zinc or triphenylphosphine. A 3-amino-2-azetidinone of formula X can be reacted as described above (i.e., first acylated and then treated as described above to introduce an

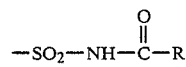

activating group in the 1-position) to yield the products of formula I wherein $R_2$ is hydrogen.

Still another synthesis for preparing the compounds of formula I wherein $R_2$, $R_3$ and $R_4$ are each hydrogen utilizes a 6-acylaminopenicillanic acid having the formula

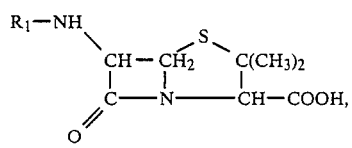

or a salt thereof, as the starting material. By adapting procedures described in the literature, 3-acylamino-2-azetidinone can be obtained from the corresponding 6-acylaminopenicillanic acid of formula XII: see, for example, Chem. Soc. Special Publication No. 28, pg. 288 (1977), The Chemistry of Penicillins, Princeton University Press, pg. 257, and Synthesis, 494 (1977).

As described in the literature 6-acylaminopenicillanic acid, or a salt thereof, can be desulfurized to yield a compound having the formula

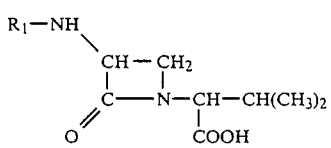

by reduction using Raney nickel. The reaction can be run in water under reflux conditions.

Replacement of the carboxyl group of a compound of formula XIV with an acetate group followed by hydrolysis yields the corresponding 3-acylamino-2-azetidinone having the formula

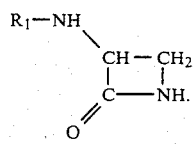  XVI

Treatment of a compound of formula XV cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

An

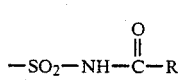

activating group can be introduced in the 1-position of a compound of formula XVI (yielding products of formula I wherein $R_2$, $R_3$ and $R_4$ are each hydrogen) using the procedures described above.

Still another variation of the abovedescribed synthetic routes for preparing a compound of formula I wherein $R_2$, $R_3$, and $R_4$ are each hydrogen comprises first desulfurizing 6-aminopenicillanic acid, acylating the resulting compound to yield a compound of formula XV and then proceeding as described above to obtain first a 3-acylamino-2-azetidinone of formula XVI and then a product of formula I.

The azetidinones of formula I wherein $R_2$ is hydrogen and at least one of $R_3$ and $R_4$ is hydrogen can also be prepared from amino acids having the formula

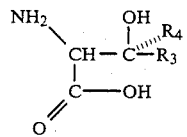  XVII (at least one of $R_3$ and $R_4$ is hydrogen). The amino group is first protected (with a protecting group "A", e.g., t-butoxycarbonyl). The carboxyl group of the protected amino acid is then reacted with an amine having the formula

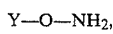  XVIII wherein Y is alkyl or benzyl, in the presence of a carbodiimide to yield a compound having the formula

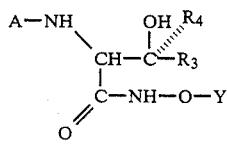  XIX (at least one of $R_3$ and $R_4$ is hydrogen). The hydroxyl group of a compound of formula XVIII is converted to a leaving group with a classical reagent, e.g., methanesulfonyl chloride (methanesulfonyl is referred to hereinafter as "Ms").

The fully protected compound having the formula

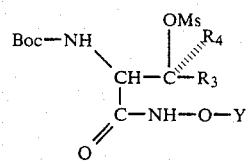  XX (at least one of $R_3$ and $R_4$ is hydrogen) is cyclized by treatment with base, e.g., potassium carbonate. The reaction is preferably carried out in an organic solvent such as acetone, under reflux conditions, and yields a compound having the formula

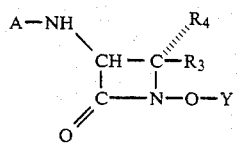  XXI (at least one of $R_3$ and $R_4$ is hydrogen).

Alternatively, cyclization of a compound of formula XIX can be accomplished without first converting the hydroxyl group to a leaving group. Treatment of a compound of formula XIX with triphenylphosphine and diethylazodicarboxylate, yields a compound of formula XXI wherein at least one of $R_3$ and $R_4$ is hydrogen.

Both of the methods disclosed above for ring closure of a compound of formula XIX result in the inversion of the stereochemistry at the carbon atom bearing the $R_3$ and $R_4$ substituents.

Removal of the protecting group from the 1-position of an azetidinone of formula XXI can be accomplished via sodium reduction when Y is alkyl, and yields an intermediate having the formula

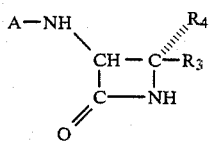  V (at least one of $R_3$ and $R_4$ is hydrogen). If Y is benzyl, catalytic (e.g., palladium on charcoal) hydrogenation will initially yield the corresponding N-hydroxy compound, which upon treatment with titanium trichloride yields an intermediate of formula VII wherein at least one of $R_3$ and $R_4$ is hydrogen.

An

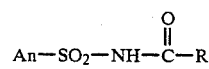

activating group can be introduced in the 1-position of a compound of formula VII using the procedures described above, and the resulting compound can be deprotected and acylated.

The starting azetidinones of formulas VII, X and XII are obtainable using any one of numerous procedures.

A 3-azido-2-azetidinone of formula XII can be prepared by first reacting an olefin having the formula

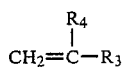   XXII with a halosulfonylisocyanate (preferably chlorosulfonylisocyanate) having the formula

   XXIII to yield an azetidinone having the formula

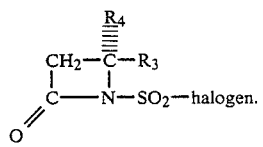   XXIV

Reductive hydrolysis of an azetidinone of formula XXIV yields an N-unsubstituted β-lactam having the formula

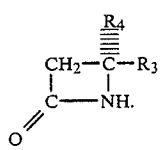   XXV

For a more detailed description of the above described reaction sequence reference can be made to the literature; see, for example, *Chem. Soc. Rev.*, 5, 181 (1976) and *J. Org. Chem.*, 35, 2043 (1970).

An azido group can be introduced in the 3-position of an azetidinone of formula XXV by reaction of the compound with an arylsulfonyl azide (such as toluenesulfonyl azide) to obtain a starting azetidinone having the formula

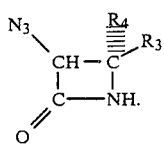   XII

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula XII.

A 3-azido-2-azetidinone of formula XII wherein R₄ is hydrogen can be prepared by first reacting a primary amine having the formula

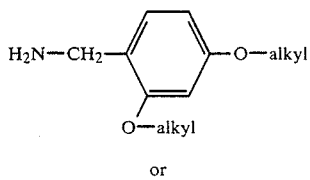   XXVIa or

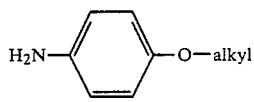   XXVIb with an aldehyde having the formula

   XXVII (or a hemiacetal) to yield the corresponding Schiff base. A [2+2] cycloaddition reaction of the Schiff base with an activated form of α-azidoacetic acid yields a 3-azido-2-azetidinone having the formula

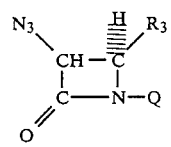   XXVIII wherein Q is

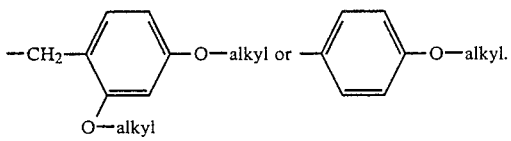

oxidative removal of the 1-substituent yields the corresponding compound having the formula

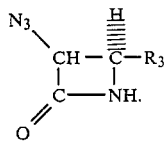   XXIX

A compound of formula VII wherein R₄ is hydrogen can be obtained using a procedure analogous to that described above for the preparation of a 3-azido-2-azetidinone of formula XII wherein R₄ is hydrogen. In place of an activated form of α-azidoacetic acid, an activated form of α-phthalimidoacetic acid is used, yielding a compound having the formula

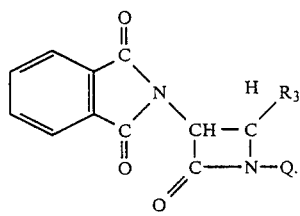   XXX

Reaction of a compound of formula XXX with a reagent such as methyl hydrazine (to cleave the phthaloyl group), followed by the introduction of a protecting group on the 3-nitrogen substituent, and oxidative removal of the 1-protecting group will yield a compound of formula VII wherein R₄ is hydrogen.

The 3-protected amino-2-azetidinones of formula VII can be obtained by first reducing a 3-azido-2-azetidinone of formula XII to obtain the corresponding 3-amino-2-azetidinone (formula X) and then introducing the amino protecting group.

The β-lactams of formula I wherein $R_2$ is methoxy can be prepared from the corresponding compound of formula I wherein $R_2$ is hydrogen. Halogenation of the amide nitrogen of a non-methoxylated compound of formula I yields an intermediate having the formula

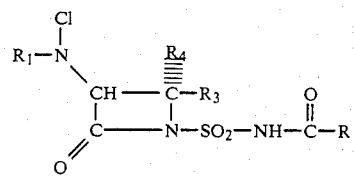
XXXI

Reagents and procedures for N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of an intermediate of formula XXXI with a methoxylating agent, e.g., an alkali metal methoxide yields a product of formula I wherein $R_2$ is methoxy in combination with its enantiomer. The reaction can be run in an organic solvent, e.g., a polar organic solvent such as dimethylformamide, at a reduced temperature.

Compounds of formula I wherein $R_2$ is methoxy can also be prepared by first methoxylating an intermediate of formula XI wherein $R_1NH$ is a carbamate (e.g., $R_1$ is benzyloxycarbonyl) and then introducing an

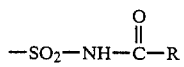

group in the 1-position of the resulting compound. Chlorination of a compound of formula XI using the procedure described above (for chlorination of a non-methoxylated compound of formula I to yield a compound of formula XXXI) yields an intermediate having the formula

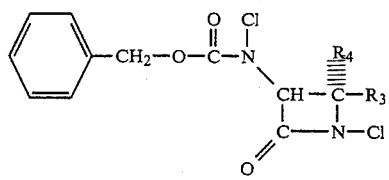
XXXII

By using the methoxylation procedure described above (for converting a compound of formula XXXI to a product of formula I), and subsequently adding a reducing agent such as trimethylphosphite, the compound of formula XXXII can be converted to an intermediate having the formula

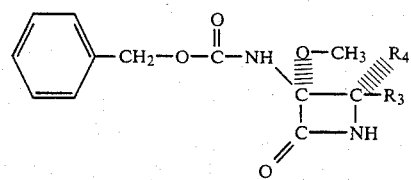
XXXIII in combination with its enantiomer when $R_3$ and $R_4$ are the same. When $R_3$ and $R_4$ are different, two diastereomeric products can be formed. An

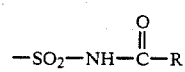

activating group can be introduced in the 1-position of a compound of formula XXXIII using the procedures described above.

Still another synthesis for preparing the products of formula I wherein $R_2$ is methoxy comprises the initial preparation of a key intermediate having the formula

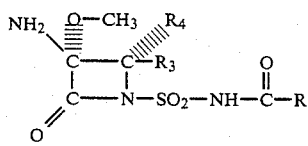
XXXIV or an intermediate of formula XXXIV in combination with its enantiomer. Such an intermediate can be obtained by reduction of a corresponding product of formula I wherein $R_1$ is benzyloxycarbonyl using catalytic (e.g., palladium on charcoal) hydrogenation. Acylation of an intermediate of formula XXXIV yields the various products of formula I wherein $R_2$ is methoxy.

The above procedures yield those products of formula I wherein $R_2$ is alkoxy, as a racemic mixture when $R_3$ and $R_4$ are the same. If desired the enantiomer having the R configuration can be isolated from the racemic mixture using conventional techniques such as fractional crystallization of a suitable salt with an optically active organic amine or by ion-paired chromatography utilizing an optically active cation.

Still another synthesis for preparing the products of formula I wherein $R_2$ is methoxy and $R_3$ and $R_4$ are hydrogen comprises the preparation of a β-lactam intermediate having the formula

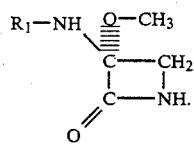
XXXV

An intermediate of formula XXXV can be obtained by first desulfurizing the corresponding 6-acylamino-6-alkoxypenicillanic acid or 7-acylamino-7-alkoxycephalosporanic acid by reduction using Raney nickel. The reaction can be run in water under reflux conditions; the resulting compound has the structural formula

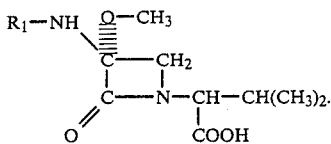

XXXVI

Replacement of the carboxyl group of the compound of formula XXXVI with an acetate group followed by hydrolysis yields a 3-acylamino-3-methoxy-2-azetidinone of formula XXXV. Treatment of a compound of formula XXXVI with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

Introduction of an

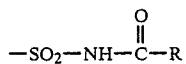

activating group in the 1-position of a compound of formula XXXV can be accomplished using the procedures described above.

The following examples are specific embodiments of this invention.

EXAMPLE 1

(S)-[1-[[(Methoxycarbonyl)amino]sulfonyl]-2-oxo-3-azetidinyl]carbamic acid, phenylmethyl ester, sodium salt (A) 1-[(1R)-Carbonyl-2-methyl(propyl)]-2-oxo-(3S)-[[phenylmethoxy)carbonyl]amino]azetidine A slurry of 6-aminopenicillanic acid (12.98 g) in 140 ml of water containing 5.18 g of sodium bicarbonate (stirred for about 10 minutes without complete solution) is added in one portion to a well-stirred (mechanical stirrer) suspension of Raney nickel (washed with water to pH 8.0, 260 ml of slurry=130 g) in a 70° C. oil bath. After 15 minutes the slurry is cooled, filtered, and the filtrate treated with 5.18 g of sodium bicarbonate and a solution of 11.94 g of benzyl chloroformate in 12 ml of acetone. After 30 minutes, the solution is acidified to pH 2.5 and extracted with methylene chloride. The organic layer is dried, evaporated, and triturated with ether/hexane to give a total of 6.83 g of the title compound.

(B) 1-(Acetyloxy)-2-methyl(propyl)]-2-oxo-(3S)-[[phenylmethoxy)carbonyl]amino]azetidine A solution of 6.83 g of 1-[(1R)-carboxy-2-methyl(-propyl)]-2-oxo-(3S)-[[(phenylmethoxy)-carbonyl]amino]azetidine in 213 ml of acetonitrile is treated with 1.95 g of cupric acetate monohydrate and 9.5 g of lead tetraacetate. The slurry is immersed in a 65° C. oil bath and stirred with a stream of nitrogen bubbling through the slurry until the starting material is consumed. The slurry is filtered and the solids washed with ethyl acetate. The combined filtrate and washings are evaporated in vacuo and the residue taken up in 100 ml each of ethyl acetate and water and adjusted to pH 7. The ethyl acetate layer is separated, dried, and evaporated to give 6.235 g of the title compound.

(C) (S)-(2-Oxo-3-azetidinyl)carbamic acid, phenylmethyl ester

A solution of 3.12 g of 1-[(acetyloxy)-2-methyl(-propyl)]-2-oxo-(3S)-[[phenylmethoxy)-carbonyl]amino]azetidine in 70 ml of methanol and 7 ml of water is cooled to −15° C. and 1.33 g of potassium carbonate and 349 mg of sodium borohydride are added. The reaction mixture is stirred at −15° C.-0° C. After the reaction is complete (about 2 hours), the mixture is neutralized to pH 7 with 2N HCl and concentrated in vacuo. The concentrate is adjusted to pH 5.8, saturated with salt and extracted with ethyl acetate (3 times). The organic layer is dried and evaporated in vacuo. The residue is combined with material from a similar experiment and triturated with ether to give 3.0 g of the title compound.

(D) (S)-[1-[[(Methoxycarbonyl)amino]sulfonyl]-2-oxo-3-azetidinyl]carbamic acid, phenylmethyl ester, sodium salt.

In a nitrogen atmosphere, 2.2 g of (S)-(2-oxo-3-azetidinyl)carbamic acid, phenylmethyl ester is suspended in 20 ml of tetrahydrofuran and 3.4 ml of monosilyltrifluoroacetamide is added. After a clear solution of the silylated starting material has formed, it is evaporated, redissolved in 20 ml absolute tetrahydrofuran and cooled to −30° C. With stirring, a solution of 2.1 g of chlorosulfonylcarbamic acid, methyl ester in 20 ml of tetrahydrofuran is added. The reaction mixture is stirred for 30 minutes at 0° C. and then for 90 minutes at room temperature and evaporated to dryness. The residue is dissolved in 50 ml of methanol, 10 ml of water is added and the mixture is adjusted to pH 6 by the addition of 2N sodium hydroxide. The methanol is removed in vacuo and the aqueous phase is extracted twice with ethyl acetate. The aqueous phase is layered with ethyl acetate and acidified with 2N hydrochloric acid. The organic phase is separated and the aqueous phase extracted once more with ethyl acetate. The combined organic phases are dried (MgSO₄) and evaporated to yield 3.4 g of the free imide of the title compound. This material is dissolved in 20 ml of methanol, filtered and 12 ml of a 1 molar solution of sodiumethylhexanoate is added. Addition of 300 ml of ether precipitates 2.5 g of the title compound, melting point 106° C., dec.

EXAMPLE 2

(3S)-[[2-Oxo-3-[[(phenylmethyl)carbonyl]amino]-1-azetidinyl]sulfonyl]carbamic acid, methyl ester, sodium salt (A) (S)-3-[[(Phenylmethyl)carbonyl]amino]-2-azetidinone (S)-3-Amino-2-azetidinone (0.86 g) is suspended in 40 ml of tetrahydrofuran and 5 ml of water is added. A solution of phenylacetic acid (1.36 g) in 10 ml of tetrahydrofuran is added, followed by N-ethyl-N'-(3-dimethylamino)propylcarbodiimide, hydrochloride (1.92 g). The solution is adjusted to pH 4 by the addition of 2N hydrochloric acid and stirred for 1 hour at room temperature. The tetrahydrofuran is removed by evaporation and the remaining suspension is filtered to yield 1 g of (S)-3-[[(phenylmethyl)carbonyl]amino]-2-azetidinone, melting point 182° C., dec.

(B) (3S)-[[2-Oxo-3-[[(phenylmethyl)carbonyl]amino]-1-azetidinyl]sulfonyl]carbamic acid, methyl ester, sodium salt (S)-3-[[(Phenylmethyl)carbonyl]amino]-2-azetidinone (0.82 g) is suspended in 20 ml of anhydrous tetrahydrofuran and 1.4 ml of monosilyltrifluoroacetamide is added to the suspension. After stirring at room temperature for 30 minutes, a clear solution forms. After 60 minutes the solution is evaporated to dryness and the residue is dissolved in 20 ml of tetrahydrofuran. At −40° C. a solution of chlorosulfonylcarbamic acid, methyl ester (0.69 g) is added dropwise with stirring. After stirring for 90 minutes at room temperature, the reaction mixture is evaporated to dryness and the residue is dissolved in 20 ml of methanol. After the addition of 5 ml water the mixture is adjusted to pH 6 by the addition of 2N sodium hydroxide. The methanol is removed by evaporation, the residue is diluted with water, extracted once with ethyl acetate, then layered with ethyl acetate and acidified with 2N hydrochloric acid. The organic phase is dried with magnesium sulfate and evaporaed to yield 0.8 g of the free amine of the title compound. The free amine of the title compound (0.7 g) is dissolved in 20 ml of methanol and 5 ml of 1N sodiumethylhexanoate is added. The resulting solution is evaporated and the residue is treated with ether to yield 0.8 g of the title compound, melting point 170° C., dec.

EXAMPLE 3

[3S(Z)]-[[3-[[(2-Amino-4-thiazolyl)(methoxyimino)acetyl]amino]-2-oxo-1-azetidinyl]sulfonyl]carbamic acid, methyl ester (A) [3S(Z)]-3-[[[2-(Triphenylmethylamino)-4-thiazolyl][methoxyimino]acetyl]amino]-2-oxoazetidine (Z)-2-(Triphenylmethylamino)-α-(methoxyimino)-4-thiazoleacetic acid (2.50 g) is dissolved in dry dimethylformamide (25 ml). 1-Hydroxybenzotriazole (863 mg), N,N'-dicyclohexylcarbodiimide (1.164 g) and 3-amino-2-oxoazetidine (485 mg) are added sequentially, and the mixture is stirred at room temperature under dry nitrogen for 5 hours. The reaction mixture is worked up by diluting it with water (250 ml) adjusting to pH 7.5, and extracting (three times) with an equal volume of ethyl acetate. The combined extract is washed with water followed by saturated aqueous sodium chloride, dried over anhydrous sodium sulfate, and evaporated to dryness in vacuo. The crude product is purified by chromatography over SilicAR CC-7 silica gel, to give 2.50 g of solid. This is crystallized from chloroform-hexane to yield 2.31 g of the title compound, melting point 233°–236° C.

(B) [3S(Z)-[[3-[[(2-Amino-4-thiazolyl)(methoxyimino)acetyl]amino]-2-oxo-1-azetidinyl]sulfonyl]carbamic acid, methyl ester

[3S(Z)]-3-[[[2-(Triphenylmethylamino)-4-thiazolyl][methoxyimino]acetyl]amino]-2-oxoazetidine (1.02 g) is suspended in 10 ml of anhydrous tetrahydrofuran monosilyltrifluoroacetamide (0.68 ml) is added to yield a solution after 10 minutes. After 30 minutes the solution is evaporated, redissolved in 10 ml of tetrahydrofuran and cooled to −30° C. At this temperature, a solution of chlorosulfonylcarbamic acid, methyl ester (0.42 g) in 5 ml of tetrahydrofuran is added. The reaction mixture is stirred for 2 hours at 0° C., then overnight at room temperature. The addition of ether precipitates 1.16 g of [3S(Z)]-[[3-[[[2-(triphenylmethylamino)-4-thiazolyl][methoxyimino]acetyl]amino]-2-oxo-1-azetidinyl]sulfonyl]carbamic acid, methyl ester; 1.1 g is dissolved in 22 ml of 70% formic acid. After stirring for 3 hours at room temperature the precipitate is removed by filtration. The filtrate is evaporated to yield 0.86 g of material which is suspended in 10 ml of water. The suspension is adjusted to pH 6.5 by the addition of 2N sodium hydroxide at 0° C., filtered and freeze-dried to yield 0.79 g of crude product. The crude product is purified by chromatography. The compound is eluted with water; 10 ml fractions are collected. From fractions 15–21, 50 mg of pure product is obtained by freeze-drying. Fractions 10–14 and 22–58 yield an additional 96 mg of less pure material.

What is claimed is:

1. A compound having the formula

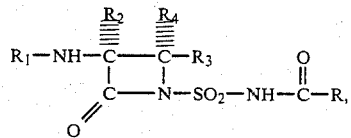

or a pharmaceutically acceptable salt thereof, wherein
R is alkyl, phenyl, substituted phenyl, phenylalkyl, (substituted phenyl)alkyl, alkoxy, phenyloxy, (substituted phenyl)oxy, phenylalkoxy, or (substituted phenyl)alkoxy;
$R_1$ is an acyl group derived from a carboxylic acid;
$R_2$ is hydrogen or methoxy;
$R_3$ and $R_4$ are the same or different and each is hydrogen or alkyl; wherein the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, or carboxyl groups.

2. A compound having the formula

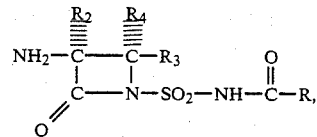

or a pharmaceutically acceptable salt thereof, wherein
R is alkyl, phenyl, substituted phenyl, phenylalkyl, (substituted phenyl)alkyl, alkoxy, phenyloxy, (substituted phenyl)oxy, phenylalkoxy, or (substituted phenyl)alkoxy;
$R_2$ is hydrogen or methoxy;
$R_3$ and $R_4$ are the same or different and each is hydrogen or alkyl; wherein the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, or carboxyl groups.

3. A compound in accordance with claim 1 or 2 wherein R is alkyl, phenyl, substituted phenyl, phenylalkyl, (substituted phenyl)alkyl, alkoxy, phenyloxy, or (substituted phenyl)alkoxy.

4. A compound in accordance with claim 1 or 2 wherein $R_3$ is alkyl and $R_4$ is hydrogen.

5. A compound in accordance with claim 1 or 2 wherein $R_2$ is hydrogen.

6. A compound in accordance with claim 1 or 2 wherein $R_3$ and $R_4$ are both hydrogen.

7. A compound in accordance with claim 1 or 2 wherein $R_3$ is hydrogen and $R_4$ is alkyl.

* * * * *